United States Patent [19]
Chong et al.

[11] Patent Number: 6,124,500
[45] Date of Patent: Sep. 26, 2000

[54] PROCESS FOR SYNTHESIZING BENZOIC ACIDS

[75] Inventors: Joshua Anthony Chong, Lansdale; Fereydon Abdesaken, Dresher; Lori Ann Spangler, Churchville; Sudhir Ramtirth Joshi, West Chester; Charles Chao Wu, North Wales, all of Pa.

[73] Assignee: Rohm and Haas Company, Phila., Pa.

[21] Appl. No.: 09/218,571

[22] Filed: Dec. 22, 1998

Related U.S. Application Data

[60] Provisional application No. 60/077,258, Mar. 9, 1998.

[51] Int. Cl.$^7$ .................................................... C07C 51/58
[52] U.S. Cl. ............................................................. 562/857
[58] Field of Search ............................................. 562/857

[56] References Cited

U.S. PATENT DOCUMENTS

| | | | |
|---|---|---|---|
| 2,511,231 | 6/1950 | Weissberger et al. | 95/6 |
| 5,530,028 | 6/1996 | Lidert et al. | 514/649 |
| 5,712,407 | 1/1998 | Krentzberger et al. | 558/283 |
| 5,792,888 | 8/1998 | Subramanian | 562/857 |

FOREIGN PATENT DOCUMENTS

| | | |
|---|---|---|
| 12496/83 | 3/1982 | Australia . |
| 0 021 121 A1 | 1/1981 | European Pat. Off. . |
| 2 089 672 | 6/1982 | United Kingdom . |

OTHER PUBLICATIONS

S. Sandler & W. Karo "Organic Functional Group Preparations." Academic Press: 1968.

M.S. Carpenter, et al., J. Org. Chem., vol. 20 (4), pp. 401–411 (1955).

T.M. Cresp, et al., J. C. S. Perkin I, pp. 2435–2447 (1974).

Nucleophilic Aromatic Substitution Reactions of Unactivated Aryl Chlorides with Methoxide Ion in Hexamethylphosphoramide, James E. Shaw, et al., *J. Org. Chem.*, vol. 41 (4), pp. 732–733 (1976).

Reaction ID 827509, *Beilstein Institut fur Literatur der organischen Chemie* (1988–1998) and *Justus Liebigs Ann. Chem.*, vol. 148, p. 222 (1868).

*Primary Examiner*—Ardin H. Marschel
*Assistant Examiner*—Sherif Kafafi
*Attorney, Agent, or Firm*—Clark R. Carpenter

[57] ABSTRACT

A nucleophilic substitution reaction on optionally substituted dihalobenzenes is carried out in the presence of an optional catalyst followed by formation of and subsequent carboxylation of a Grignard reaction intermediate. In particular the present invention provides a process leading to optionally substituted hydroxybenzoic, alkanoyloxybenzoic, formyloxybenzoic and alkoxybenzoic acids from 1-substituted 2,6-dihalobenzenes. The invention also provides a process for the direct formation of an acyl chloride from a Grignard reagent by quenching with phosgene.

7 Claims, No Drawings

PROCESS FOR SYNTHESIZING BENZOIC ACIDS

This application claims benefit of provisional application Ser. No. 60/077,258 filed Mar. 9, 1998.

The present invention relates to processes for the manufacture of aromatic carboxylic acids or acid chlorides having an alkoxy, hydroxy, formyloxy or alkanoyloxy substitutent on the aromatic ring.

In particular, benzoic acids with an alkoxy, hydroxy, formyloxy or alkanoyloxy substitutent on the aromatic ring are used for various commercial applications including the manufacture of agricultural and pharmaceutical chemicals. In many instances, the use of acid chlorides is especially convenient for the formation of amides or hydrazides which are useful for such chemicals. Although various routes are known, for example, conversion of an amino substituted benzoic acid or ester to an alkoxy or hydroxy substituted benzoic acid or ester using a diazotization reaction as described in U.S. Pat. No. 5,530,028, or the hydrolysis of 3-methoxy-2-methylbenzonitrile to 3-methoxy-2-methylbenzoic acid as described by M. S. Carpenter et al. in *J. Org. Chem.* 20 (4), 401–411 (1955), there is a continuing need to provide these kinds of acids at lower cost and higher purity in processes requiring a lesser number of steps or operations. Additionally, even though the conversion of 6-chloro-2-methoxytoluene to 3-methoxy-2-methylbenzoic acid using Grignard reaction conditions is described in AU-A-12496/83, the yield is lower in the example given than are yields in the present invention which comprises a Grignard reaction. Thus, the present invention provides an advantageous routes to produce the desired benzoic acids.

Furthermore, we have discovered that phosgene may be used as a quenching agent for a Grignard reagent to provide the benzoyl chloride directly without the necessity of first isolating the benzoic acid and then subsequently chlorinating it using thionyl chloride, a phosphorous chloride or other chlorinating reagent with its subsequent problems of sulfur or phosphorous by-product disposal.

One embodiment of this invention provides a process for the preparation of a compound of formula (III) comprising the steps of (i) reacting a compound of formula (I) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to form a compound of formula (IIa)

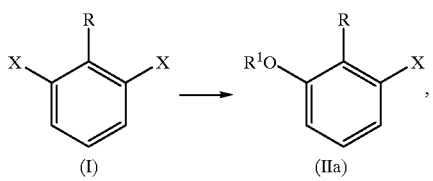

(ii) reacting a compound of formula (IIa) with magnesium metal using anhydrous conditions to form an intermediate compound of formula (IIb)

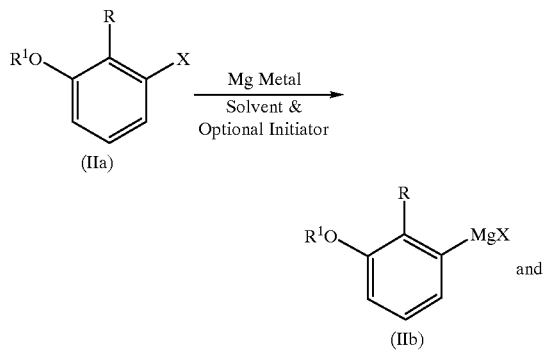

(iii) reacting the intermediate compound of formula (IIb) with carbon dioxide to form a compound of formula (III) after hydrolysis

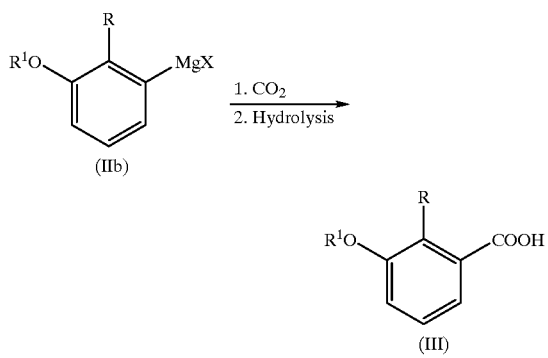

wherein
each X is independently chloro, bromo or iodo;
R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$alkyl, aryl, aryl$(C_1–C_2)$alkyl, heteroaryl or heteroaryl$(C_1–C_2)$alkyl substituted with from one to three substituents independently selected from $(C_1–C_3)$alkyl and $(C_1–C_3)$alkoxy;
$R^1$ is $CHR^2R^3$, aryl, aryl$(C_1–C_2)$alkyl or heteroaryl$(C_1–C_2)$alkyl; or aryl, aryl$(C_1–C_2)$alkyl or heteroaryl$(C_1–C_2)$alkyl substituted with from one to three substituents independently selected from $(C_1–C_3)$alkyl and $(C_1–C_3)$alkoxy; and
$R^2$ and $R^3$ are each independently a hydrogen atom, $(C_1–C_5)$alkyl or $(C_1–C_3)$alkyl substituted with $(C_1–C_2)$alkoxy.

This embodiment further provides a process for the preparation of a compound of formula (IV) comprising the additional step of (iv) hydrolyzing a compound of formula (III) using an ether cleavage reagent

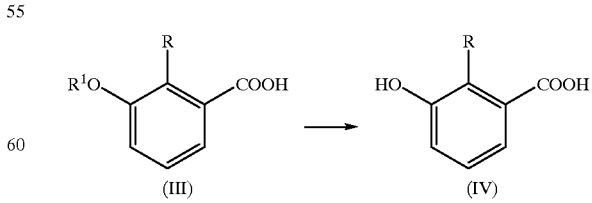

wherein
R is a hydrogen atom, $(C_1–C_6)$alkyl, aryl, aryl$(C_1–C_2)$alkyl, heteroaryl or heteroaryl$(C_1–C_2)$alkyl; or a $(C_1–C_6)$ alkyl, aryl, aryl($C_1$–$C_2$)alkyl, heteroaryl or heteroaryl ($C_1$–$C_2$)alkyl substituted with from one to three substituents independently selected from ($C_1$–$C_3$)alkyl and ($C_1$–$C_3$)alkoxy;

$R^1$ is $CHR^2R^3$, aryl, aryl($C_1$–$C_2$)alkyl or heteroaryl ($C_1$–$C_2$)alkyl; or aryl, aryl($C_1$–$C_2$)alkyl or heteroaryl ($C_1$–$C_2$)alkyl substituted with from one to three substituents independently selected from ($C_1$–$C_3$)alkyl and ($C_1$–$C_3$)alkoxy; and $R^2$ and $R^3$ are each independently a hydrogen atom, ($C_1$–$C_5$)alkyl or ($C_1$–$C_3$)alkyl substituted with ($C_1$–$C_2$)alkoxy.

This embodiment still further provides a process for the preparation of a compound of formula (V) comprising the second additional step of (v) reacting a compound of formula (IV) with an organic acid anhydride

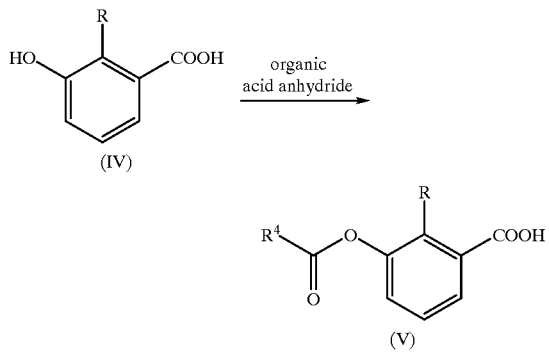

wherein

R is a hydrogen atom, ($C_1$–$C_6$)alkyl, aryl, aryl($C_1$–$C_2$) alkyl, heteroaryl or heteroaryl($C_1$–$C_2$)alkyl; or a ($C_1$–$C_6$) alkyl, aryl, aryl($C_1$–$C_2$)alkyl, heteroaryl or heteroaryl ($C_1$–$C_2$)alkyl substituted with from one to three substituents independently selected from ($C_1$–$C_3$)alkyl and ($C_1$–$C_3$) alkoxy;

$R^4$ is a hydrogen atom or ($C_1$–$C_3$)alkyl; and the organic acid anhydride is formic anhydride, acetic anhydride, a propionic anhydride or a butyric anhydride.

This embodiment further embraces all the previously described process steps leading to compounds of formula (III), (IV), and (V) wherein the starting materials is a compound of formula (IIa) rather than a compound of formula (I). In all cases, the compound of formula (III) can be converted to the corresponding acid chloride (VII), if desired, using reactants known to one of ordinary skill in the art, for example, thionyl chloride:

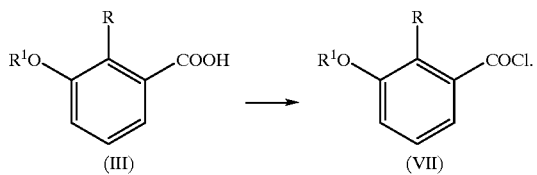

In a second embodiment of this invention, the Grignard reaction may be conveniently effected on a compound of formula (I) as the first step of the process. Therefore, this second embodiment provides a process for the preparation of a compound of formula (III) comprising the steps of (i) reacting a compound of formula (I) with magnesium metal using anhydrous conditions to form an intermediate compound of formula (VIa)

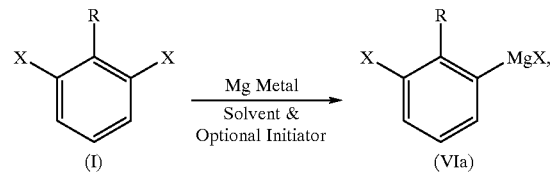

(ii) reacting the intermediate compound of formula (VIa) with carbon dioxide to form a compound of formula (VIb) after hydrolysis

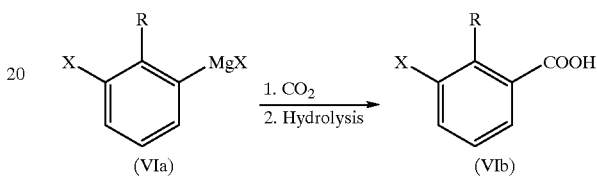

and (iii) reacting a compound of formula (VIb) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to form a compound of formula (III)

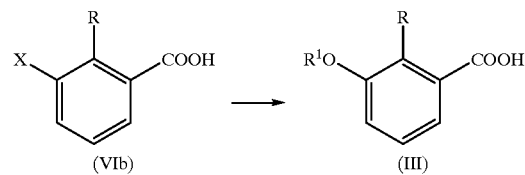

wherein each X is independently chloro, bromo or iodo;

R is a hydrogen atom, ($C_1$–$C_6$)alkyl, aryl, aryl($C_1$–$C_2$) alkyl, heteroaryl or heteroaryl($C_1$–$C_2$)alkyl; or a ($C_1$–$C_6$) alkyl, aryl, aryl($C_1$–$C_2$)alkyl, heteroaryl or heteroaryl ($C_1$–$C_2$)alkyl substituted with from one to three substituents independently selected from ($C_1$–$C_3$)alkyl and ($C_1$–$C_3$) alkoxy;

$R^1$ is $CHR^2R^3$, aryl, aryl($C_1$–$C_2$)alkyl or heteroaryl ($C_1$–$C_2$)alkyl; or aryl, aryl($C_1$–$C_2$)alkyl or heteroaryl ($C_1$–$C_2$)alkyl substituted with from one to three substituents independently selected from ($C_1$–$C_3$)alkyl and ($C_1$–$C_3$) alkoxy; and $R^2$ and $R^3$ are each independently a hydrogen atom, ($C_1$–$C_5$)alkyl or ($C_1$–$C_3$)alkyl substituted with ($C_1$–$C_2$) alkoxy.

This second embodiment further provides a process for the preparation of a compound of formula (IV) comprising the additional step of (iv) hydrolyzing a compound of formula (III) using an ether cleavage reagent

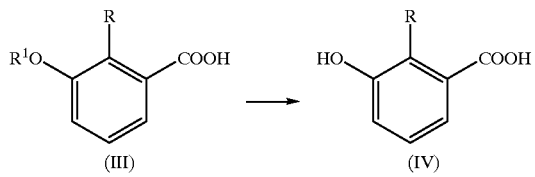
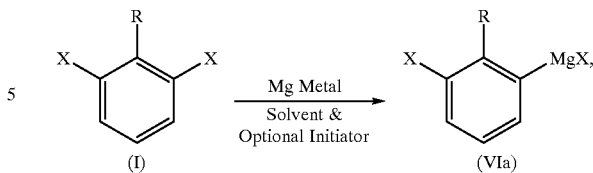

wherein

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl $(C_1-C_2)$alkyl substituted with from one to three substituents independently selected from $(C_1-C_3)$alkyl and $(C_1-C_3)$alkoxy;

$R^1$ is $CHR^2R^3$, aryl, aryl$(C_1-C_2)$alkyl or heteroaryl $(C_1-C_2)$alkyl; or aryl, aryl$(C_1-C_2)$alkyl or heteroaryl $(C_1-C_2)$alkyl substituted with from one to three substituents independently selected from $(C_1-C_3)$alkyl and $(C_1-C_3)$alkoxy; and $R^2$ and $R^3$ are each independently a hydrogen atom, $(C_1-C_5)$alkyl or $(C_1-C_3)$alkyl substituted with $(C_1-C_2)$alkoxy.

This second embodiment still further provides a process for the preparation of a compound of formula (V) comprising the second additional step of (v) reacting a compound of formula (IV) with an organic acid anhydride

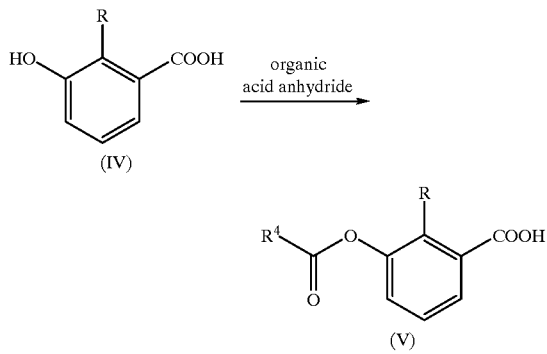

wherein

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl $(C_1-C_2)$alkyl substituted with from one to three substituents independently selected from $(C_1-C_3)$alkyl and $(C_1-C_3)$alkoxy;

$R^4$ is a hydrogen atom or $(C_1-C_3)$alkyl; and the organic acid anhydride is formic anhydride, acetic anhydride, a propionic anhydride or a butyric anhydride.

In a variant of the second embodiment of this invention, the compound of formula (IV) is produced directly from the compound of formula (VIb). Therefore, this variant of second embodiment provides a process for the preparation of a compound of formula (IV) comprising the steps of (i) reacting a compound of formula (I) with magnesium metal using anhydrous conditions to form an intermediate compound of formula (VIa)

(ii) reacting the intermediate compound of formula (VIa) with carbon dioxide to form a compound of formula (VIb) after hydrolysis

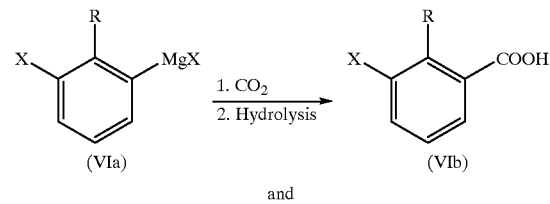

and (iii) reacting a compound of formula (VIb) with sodium hydroxide, potassium hydroxide, lithium hydroxide or a mixture thereof, optionally in the presence of a catalyst comprising copper, to form a compound of formula (IV)

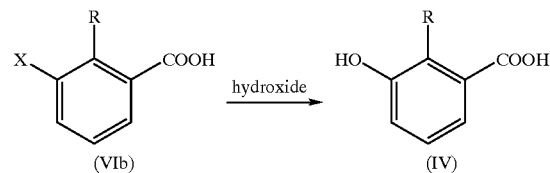

wherein each X is independently chloro, bromo or iodo and

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl $(C_1-C_2)$alkyl substituted with from one to three substituents independently selected from $(C_1-C_3)$alkyl and $(C_1-C_3)$alkoxy.

This variant of the second embodiment further provides a process for the preparation of a compound of formula (V) comprising the additional step of (iv) reacting a compound of formula (IV) with an organic acid anhydride

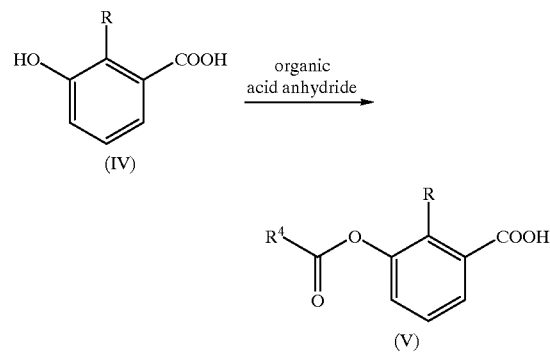

wherein

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$ alkyl, aryl, aryl($C_1$–$C_2$)alkyl, heteroaryl or heteroaryl ($C_1$–$C_2$)alkyl substituted with from one to three substituents independently selected from ($C_1$–$C_3$)alkyl and ($C_1$–$C_3$) alkoxy;

$R^4$ is a hydrogen atom or ($C_1$–$C_3$)alkyl; and the organic acid anhydride is formic anhydride, acetic anhydride, a propionic anhydride or a butyric anhydride.

In a third embodiment of this invention, the Grignard reaction may be conveniently effected on a compound of formula (II) using phosgene as a quenching agent to provide directly an acid chloride compound of formula (VII). Therefore, this third embodiment provides a process for the preparation of a compound of formula (VII) comprising the steps of (i) reacting a compound of formula (I) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to form a compound of formula (IIa)

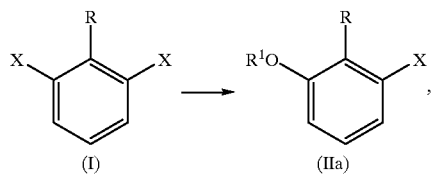

(ii) reacting a compound of formula (IIa) with magnesium metal using anhydrous conditions to form an intermediate compound of formula (IIb)

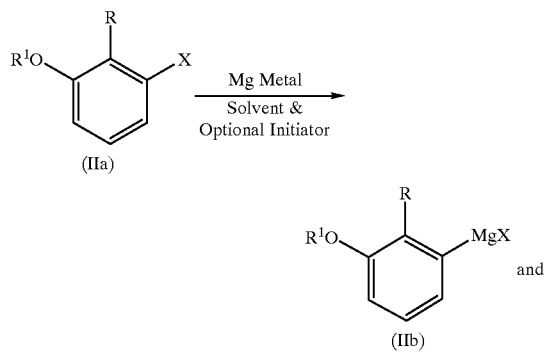

(iii) reacting the intermediate compound of formula (IIb) with phosgene to form a compound of formula (VII)

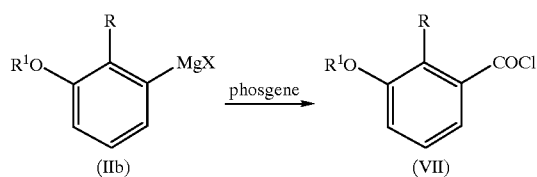

wherein each X is independently chloro, bromo or iodo;

R is a hydrogen atom, ($C_1$–$C_6$)alkyl, aryl, aryl($C_1$–$C_2$) alkyl, heteroaryl or heteroaryl($C_1$–$C_2$)alkyl; or a ($C_1$–$C_6$) alkyl, aryl, aryl($C_1$–$C_2$)alkyl, heteroaryl or heteroaryl ($C_1$–$C_2$)alkyl substituted with from one to three substituents independently selected from ($C_1$–$C_3$)alkyl and ($C_1$–$C_3$) alkoxy;

$R^1$ is $CHR^2R^3$, aryl, aryl($C_1$–$C_2$)alkyl or heteroaryl ($C_1$–$C_2$)alkyl; or aryl, aryl($C_1$–$C_2$)alkyl or heteroaryl ($C_1$–$C_2$)alkyl substituted with from one to three substituents independently selected from ($C_1$–$C_3$)alkyl and ($C_1$–$C_3$) alkoxy; and $R^2$ and $R^3$ are each independently a hydrogen atom, ($C_1$–$C_5$)alkyl or ($C_1$–$C_3$)alkyl substituted with ($C_1$–$C_2$) alkoxy.

The present invention is summarized conveniently by Diagram 1 hereinbelow.

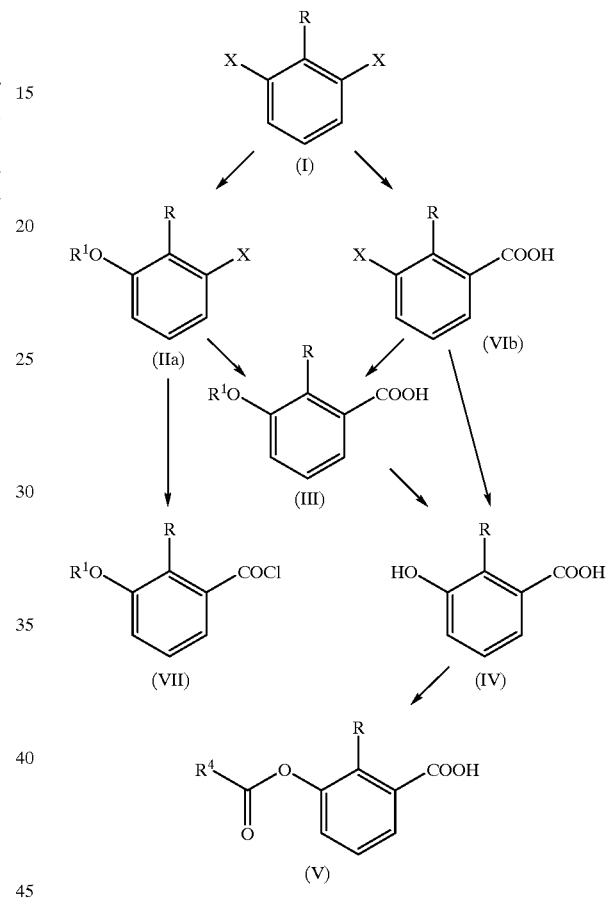

In all the process embodiments of this invention described previously, preferred processes are those wherein each X is independently chloro or bromo;

R is a hydrogen atom or ($C_1$–$C_6$)alkyl;

$R^1$ is $CHR^2R^3$, aryl or aryl($C_1$–$C_2$)alkyl;

$R^2$ and $R^3$ are each independently a hydrogen atom or ($C_1$–$C_2$)alkyl, or ($C_1$–$C_2$)alkyl substituted with methoxy; and $R^4$ is ($C_1$–$C_3$)alkyl.

More preferred processes are those wherein each X is chloro, R is a hydrogen atom or ($C_1$–$C_3$)alkyl, $R^1$ is $CHR^2R^3$, $R^2$ and $R^3$ are each independently a hydrogen atom or ($C_1$–$C_2$)alkyl, and $R^4$ is ($C_1$–$C_2$)alkyl.

Even more preferred processes are those wherein R is methyl or ethyl, $R^2$ is a hydrogen atom, $R^3$ is a hydrogen atom or methyl, and $R^4$ is methyl.

In a fourth embodiment of this invention, a process is provided for the direct formation of an acyl chloride of formula (IX) by quenching a Grignard reagent of formula (VIII) with phosgene

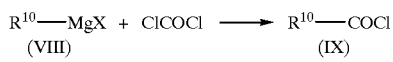

wherein $R^{10}$ is an organic radical selected from alkyl, aryl and aralkyl, and X is chloro, bromo or iodo.

As used herein, the term "alkyl" refers to straight and branched aliphatic hydrocarbon chains, for example, methyl, ethyl, n-propyl, isopropyl, n-butyl, sec-butyl, tert-butyl, isoamyl and n-hexyl.

The term "alkoxy" refers to straight and branched aliphatic hydrocarbon chains attached to an oxygen atom, for example, methoxy, ethoxy, n-propoxy, isopropoxy and the like.

The term "aryl" refers to an aromatic ring system, for example, phenyl, 1-naphthyl, 2-naphthyl and the like which may be substituted with one or more alkyl and halo groups.

The term "aralkyl" refers to an aryl group which is attached to an alkylene group, for example, benzyl, phenethyl and the like, the aryl portion of which may be substituted with one or more alkyl and halo groups.

The term "heteroaryl" refers to aromatic heterocyclic groups. Heteroaryl rings and the heteroaryl moieties of other groups, such as heteroarylalkyl, are typically 5 or 6 membered aromatic rings containing one or more O, N, or S atoms which may be fused to one or more other aromatic, heteroaromatic or heterocyclic rings such as a benzene ring. Examples of heteroaryl groups include, but are not limited to, thienyl, furyl, pyrrolyl, triazolyl, thiazolyl, oxazolyl, isoxazolyl, thiazolyl, isothiazolyl, pyridyl, pyrimidinyl, pyrazinyl, pyridazinyl, triazinyl, benzofuranyl, benzothienyl, indolyl, quinazolinyl, acridinyl, purinyl and quinoxalinyl.

The term "heteroarylalkyl" refers to a heteroaryl group which is attached to an alkylene group, for example, furfuryl, thenyl, nicotinyl and the like.

The term "alkali" refers to a lithium, potassium or sodium atom.

The term "alkaline earth" refers to a magnesium, calcium, barium or strontium atom.

The monoalkoxylation or monoaroxylation reaction, which is used to convert a compound of formula (I) to a compound of formula (IIa) or a compound of formula (VIb) to a compound of formula (III) can be performed with or without a catalyst being present. If no catalyst is employed, the preferred solvent is dimethyl sulfoxide (DMSO). When a catalyst is employed, suitable ones comprise copper and include copper(I) chloride, copper(I) bromide, copper(I) iodide, copper(I) cyanide, copper(II) chloride, copper(II) oxide, copper(II) sulfate and elemental copper. Copper(I) cyanide is a preferred catalyst. The catalyst comprising copper can be in many forms such as powders or copper deposited on carriers of which powders are especially preferred. When the catalyst is utilized, the usage rate is from 0.1 to 100 mole percent, based on the compound of formula (I) or (VIb). The preferred usage rate is from 0.5 to 25 mole percent. A more preferred usage rate is from 1 to 10 mole percent.

There are many suitable carriers which can be used to support the copper catalyst including, but not limited to, silica, carbon, alumina, calcium carbonate and the like.

Suitable alkali and alkaline earth alkoxide reagents, used to convert a compound of formula (I) to a compound of formula (IIa) or a compound of formula (VIb) to a compound of formula (III) include, but are not limited to, sodium methoxide, potassium methoxide, sodium ethoxide, magnesium methoxide, barium methoxide, calcium ethoxide, strontium ethoxide and the like. Similarly, suitable alkali and alkaline earth aroxides include sodium phenoxide, potasium phenoxide, lithium phenoxide, calcium phenoxide, magnesium phenoxide and the like. Suitable alkali and alkaline earth arylalkoxides include sodium benzoxide, calcium benzoxide and the like. Suitable alkali and alkaline earth heteroarylalkoxides include potassium thenoxide and the like. The alkali and alkaline earth alkoxides, aroxides, arylalkoxides and heteroarylalkoxides are usually used in the amount of from 100 to 200 mole percent based upon the aromatic compound substituted with halo.

The process of this invention permits the selective replacement of a single halo group on the aromatic ring of a compound of formula (I) with an alkoxy, aroxy, arylalkoxy or heteroarylalkoxy group. As an example, the present invention is able to monoalkoxylate, monoaroxylate, monoarylalkoxylate or monoheteroarylalkoxylate a 1-alkyl-2,6-dihalobenzene to a 1-alkyl-6-(alkoxy or aroxy or arylalkoxy or heteroarylalkoxy)-2-halobenzene with greater than 80% selectivity. Using preferred conditions, the selectivity is greater than 85%. Under more preferred conditions, the selectivity is greater than 90%. As is known to those of ordinary skill in the art, higher selectivities are commonly achieved at lower conversions. For example, when 2,6-dichlorotoluene is reacted with a methoxide, the selectivity to 6-chloro-2-methoxytoluene is greater than 99% at 70% conversion. When the conversion increases to 93%, the selectivity decreases to about 95%.

The reaction rate for the displacement of a single halo group is enhanced if a suitable solvent or mixture of solvents is employed. Dimethylformamide (DMF), DMSO, 1-methyl-2-pyrrolidinone (NMP), dimethyl sulfate (DMS), ethyl acetate and suitable alcohols, such as methanol and ethanol, are preferred solvents, with DMSO and NMP being more preferred. DMSO is the most preferred solvent. The reaction is usually conducted at a temperature from 65 to 160° C., preferably higher than 90° C.

The conversion of compounds of formula (VIb) to compounds of formula (IV) is generally carried out under process conditions similar to those used to convert a compound of formula (I) to a compound of formula (IIa) or a compound of formula (VIb) to a compound of formula (III) except that a hydroxide is used in place of the organic oxide. Polar solvents, for example DMSO, NMP, DMF, methanol, and ethanol or mixtures thereof, can be used to dissolve all the reagents. Preferred solvents are DMSO and NMP. The reaction can be run with or without a copper catalyst. Copper catalysts include cuprous cyanide, cuprous bromide and other Cu (I) salts. The hydroxide can have any desired metal counterion. Preferred are lithium, sodium, potassium or mixtures thereof. The addition order of reagents is not critical. The reaction temperature is generally 100–160° C., preferably 140–160° C.

The Grignard reaction, which is used either to convert a compound of formula (IIa), the aryl halide, to a compound of formula (IIb), the Grignard intermediate, or to convert a compound of formula (I), the aryl dihalide to a compound of formula (VIa), the mono-Grignard intermediate, is performed under anhydrous conditions. The presence of water can sharply attenuate the formation of desired product since it reacts with the Grignard intermediate to produce a 1,2-disubstituted benzene:

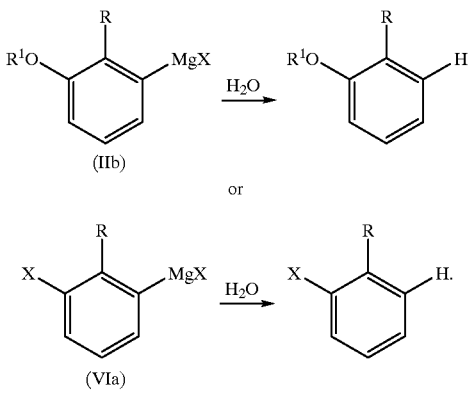

(IIb)

or (VIa)

A convenient temperature for the reaction is the reflux temperature of the aryl halide plus solvent combination. Temperatures of from about 60° C. to about 115° C. are preferred. Pressure is customarily ambient for convenience, but super-atmospheric pressure with resultant higher attendant reaction temperatures can be used if desired. Because of the chemical nature of the aryl halide, the reaction times are somewhat longer than those sometimes employed to form Grignard reagents. However, the formation of the mono-Grignard salt of formula (VIa) from the compound of formula (I) is somewhat more facile than the formation of the Grignard salt of formula (IIb) from the compound of formula (IIa). In order to attain a high conversion to the Grignard intermediate, reaction times usually are from about 5 hours to about 24 hours, preferably from about 7 hours to about 10 hours. In order to facilitate the reaction, the magnesium metal should be free of magnesium oxide build-up on the surface of the metal. An excess of magnesium is generally used in relation to the aryl halide. In batch processes, from about a 1% to about 50% excess, preferably from about 5% to about 20% excess, of magnesium is used per equivalent of aryl halide. The solvent employed is usually an ether although an aromatic hydrocarbon such as toluene or xylene can be used. A solvent mixture comprising an ether and an aromatic hydrocarbon can be used if desired. The ether is preferably an ether containing 6–12 carbon atoms such as di-n-butyl ether, a multiple oxy ether such as bis(2-methoxyethyl) ether (diglyme), or a cyclic ether such as tetrahydrofuran (THF). THF is a preferred solvent. The amount of solvent used is not overly important and can be from about 1 to about 10 equivalents based on the aryl halide. When aryl chlorides, for example 6-chloro-2-methoxytoluene or 2,6-dichlorotoluene, are used, a small amount of an initiator such as 1,2-dibromoethane, an alkyl iodide or alkyl bromide can optionally be present in the reaction mixture to minimize the time required for the reaction to start. Usually from about 0.01 to about 0.05 equivalent of initiator based on the aryl halide is sufficient. Alternatively, in batch procedures, a small amount of Grignard intermediate from the preceding batch (an activated heel) can be employed as the initiator. A process may also be used whereby a solution of the aryl halide of formula (I) or (IIa) is passed through a column of magnesium particles in order to continuously generate a solution of the Grignard reagent.

The carboxylation reaction is followed by hydrolysis either to convert a compound of formula (IIb) to a compound of formula (III) or to convert a compound of formula (VIa) to a compound of formula (VIb). The carboxylation reaction itself is also carried out under anhydrous conditions in order to avoid the formation of the by-product as noted hereinbefore. The reaction can be performed using any anhydrous source of carbon dioxide. That is, the dry carbon dioxide, either from a gas cylinder or from sublimed dry ice, can be bubbled through the Grignard solution. A moderate to low carbon dioxide flow rate is preferred. Alternatively, the Grignard solution may be poured onto dry ice in an anhydrous condition or anhydrous dry ice can be added to the Grignard solution. Still another means of conducting the reaction is to maintain a carbon dioxide atmosphere at either atmospheric or super-atmospheric pressure during the formation of the initial Grignard intermediate. An excess amount relative to the Grignard intermediate of carbon dioxide is conveniently employed. Because the Grignard carboxylate salt, shown hereinbelow, is quite viscous and insoluble, it

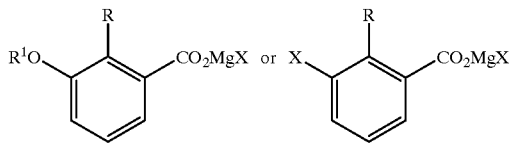

is frequently advantagous to add additional anhydrous solvent to the mixture in order to retain stirring capability. The yield of the desired Grignard carboxylate salt is enhanced if the reaction is kept cold. A reaction temperature at or about 0° C. is preferred. Reaction time depends upon the rate of carbon dioxide admittance, the reactor characteristics, the solvent employed, the temperature of the reaction mixture, and the structure of the compound of formula (IIb) or formula (VIa). However, a time of from about 30 minutes to about 5 hours is generally preferred when the anhydrous carbon dioxide is bubbled into the Grignard solution.

The resulting Grignard carboxylate salt is readily converted to the carboxylic acid compound of formula (III) or formula (VIb) by hydrolysis using water or aqueous acid in normal fashion known to those of ordinary skill in the art.

For the direct conversion of compounds of formula (IIa) to compounds of formula (VII) using phosgene as the Grignard quenching agent, the formation of the Grignard salt is initiated with iodomethane. Other haloalkanes are also suitable for the initiation, for example, dibromoethane. Alternatively, the reaction can be initiated by cutting or grinding the magnesium metal to give a fresh surface. Preferably, it is initiated by adding a heel of a previous Grignard reaction on the same material, before that reaction was quenched. The Grignard formation reaction takes place at a temperature of from 80 to 160° C., preferably from 90 to 115° C.

The solvents used for the Grignard must be non-reactive to the Grignard conditions and somewhat polar to dissolve reagents, for example, THF and other ethers. After solution is attained, a higher boiling, inert solvent can be added to raise the temperature so the Grignard will form. Solvents suitable in this regard include any non-reactive alkane, ether or aromatic compound such as toluene.

The phosgene addition can be carried out at any temperature below the boiling point of phosgene, or at higher temperatures if the vessel was allowed to be pressurized during the addition of phosgene, or with a very cold condenser to keep the phosgene in the reactor. Normally, at ambient pressure, the phosgene is added at −30 to 30° C. Higher temperatures are acceptable when a pressure vessel is employed.

Phosgene can be used in a stoichiometric amount of from 1.1 to 10 equivalents per equivalent of the formed Grignard intermediate with from 1.1 to 3 equivalents being preferred.

The ether cleavage reaction can be conducted using reactions known to those with ordinary skill in the art. For example, this reaction is performed by heating a compound of formula (III) with a Bronsted acid, for example, hydrochloric acid, hydrobromic acid, hydroiodic acid, sulfuric acid and trifluoroacetic acid, with a Lewis acid, for example, boron trifluoride etherate, aluminum trichloride or magnesium chloride, with a base such as sodium methoxide, pyridine or methylamine, or with a strong acid-weak base salt such as pyridine hydrochloride to form a hydroxy substituted compound of formula (IV). Appropriate reaction temperatures can be from ambient to over 200° C.

The reaction of a compound of formula (IV) with an organic acid anhydride to form a compound of formula (V) is generally performed at a reaction temperature of from about 0° C. to about 150° C., preferably from about 10° C. to about 100° C. and more preferably from about 15° C. to about 75° C. Any solvent which does not participate in the desired esterification reaction is acceptable. The esterification can be run with or without a catalyst being present. When a catalyst is employed, it is most usually selected from a tertiary amine, for example pyridine, quinoline, a picoline, N-methylpyrrole, N-methylpyrrolidine or a trialkylamine such as triethylamine. Preferred catalysts are pyridine and triethylamine.

The following examples and experimental procedures are provided for additional guidance to the practitioner.

EXAMPLE 1

Methoxylation of 2,6-Dichlorotoluene (DCT) to 6-Chloro-2-methoxytoluene (MCT)

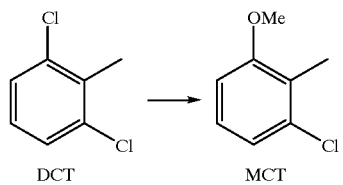

Me = methyl

To a 500 milliliter (mL) flask, equipped with a temperature controller, a condenser, and a magnetic stirrer, were charged 50 grams (g) of DCT (0.31 mol), 30 g of 95% potassium methoxide (0.41 mol), and 25 g of 1-methyl-2-pyrrolidinone (NMP). The mixture was stirred at 100° C. for 2 hours, and then at 120° C. for 18 hours. Dimethyl sulfate (10 g, 0.08 mol) was then added, and the resulting mixture was further stirred at 120° C. for 5 hours. After this period, the mixture was cooled to ambient temperatures and filtered. The filter cake was washed with isopropanol (3×65 mL). Analysis of the combined filtrate and washes showed that 40 g of MCT was generated. Yield: 82%.

EXAMPLE 2

Methoxylation of DCT Using CuCN in DMF

To a 25 mL flask, equipped with a temperature controller, a condenser, and a magnetic stirrer, were charged 2.00 g of DCT (12.4 mmol), 1.30 g of NaOCH$_3$ (24.1 mmol), 0.10 g of CuCN (1.2 mmol), and 10.0 g of DMF. The mixture was heated to 120° C. and stirred under nitrogen. Gas chromatography (GC) analysis showed that after 17 hours, the yield of MCT was 88.6%, with 10.0% of DCT left. The yield of MCT increased to 92.8% after 19 hours, with 1.4% of DCT still unreacted.

EXAMPLE 3

Methoxylation of DCT Using CuCN in DMF

To a 25 mL flask, equipped with a temperature controller, a condenser, and a magnetic stirrer, were charged 5.00 g of DCT (31.0 mmol), 2.00 g of NaOCH$_3$ (37.0 mmol), 0.15 g of CuCN (1.7 mmol), and 5.00 g of DMF. The mixture was heated to 150° C. and stirred under nitrogen. GC analysis showed that after 17 hours, the yield of MCT was 64.8%, with 28.1% of DCT left. The yield of MCT increased to 76.0% after 26 hours, when 16.3% of DCT was still unreacted.

EXAMPLE 4

Methoxylation of DCT Using CuCN in DMSO

To a 25 mL flask, equipped with a temperature controller, a condenser, and a magnetic stirrer, were charged 5.00 g of DCT (31.0 mmol), 2.00 g of NaOCH$_3$ (37.0 mmol), 0.15 g of CuCN (1.7 mmol), and 5.0 g of DMSO. The mixture was heated to 140° C. and stirred under nitrogen. GC analysis showed that after 6 hours, the yield of MCT was 82.8%, with 12.4% of DCT left. The yield of MCT increased to 86.1% after 12 hours, when 7.2% of DCT was still unreacted.

EXAMPLE 5

Methoxylation of DCT Using CuBr in Methanol

To a 25 mL flask, equipped with a thermometer, a condenser, and a magnetic stirrer, were charged 2.00 g of DCT (12.4 mmol), 5.00 g of 25% NaOCH$_3$ solution (in methanol, 23.1 mmol), 0.25 g of CuBr (1.7 mmol), and 0.44 g of ethyl acetate. The mixture was heated to reflux and stirred under nitrogen. GC analysis showed that after 5 hours, the yield of MCT was 7.3%, with 92.1% of DCT left. The yield of MCT increased to 25.2% after 24 hours, when 65.2% of DCT was still unreacted.

EXAMPLE 6

Methoxylation of DCT in DMSO

EXAMPLE 6A

To a 3-necked flask equipped with a reflux condenser, a mechanical stirrer and a temperature controller was charged DCT (483 g), DMSO (193 g) and sodium methoxide (154 g). The mixture was purged with nitrogen, then heated to 140–160° C. with stirring under a nitrogen blanket. The reaction was stopped when the residual DCT was <23%, usually in 4–6 h. The mixture was then distilled under reduced pressure (15–20 mm Hg) using a 10-tray Oldershaw column, and about 300 g of distillate was removed (pot temperature 100–120° C.), head temperature 75–100° C.). To the pot residue was added dimethyl sulfate (DMS, 18 g) and this mixture held at 120° C. for 1 h. Water (400 g) was added to the flask and stirred at 75° C. for 30 min. After phase separation, the lower aqueous phase was removed and discarded. The crude product may be washed, if desired, with dilute hydrogen peroxide solution to oxidize any impurities and/or remove any odor. The product MCT can be collected by distillation, or dried and used in a subsequent Grignard reaction. The MCT yield was >94%, based on DCT consumption.

The 300 g distillate from above consisted of DMSO (50–60%), DCT (25–40%), and MCT (10–25%) and can be recycled directly into the next methoxylation batch.

EXAMPLE 6B

As Example 6A above, but sodium methoxide was added in several portions in order to control any exotherm.

EXAMPLE 6C

As Example 6A above, but the reaction was carried out until the residual DCT was 6–10%.

EXAMPLE 7

Methoxylation of DCT in DMSO

To a 3-necked flask equipped with a reflux condenser, a mechanical stirrer and a temperature controller was charged DCT (483 g), DMSO (93 g) and sodium methoxide (154 g). The mixture was purged with nitrogen, then heated to 140–160° C. with stirring under a nitrogen blanket. The reaction was stopped when the residual DCT was <23%, usually in 4–6 h. Water (400 g) was added to the flask and stirred at 75° C. for 30 min. After phase separation, the lower aqueous phase was removed and discarded. The product was washed again with water. The crude product was washed with dilute hydrogen peroxide solution to oxidize any impurities and/or remove any odor. The product MCT can be collected by distillation, then dried and used in a subsequent Grignard reaction.

EXAMPLE 8

Grignard Reaction to Convert MCT to 3-Methoxy-2-methylbenzoic Acid (MMBA)

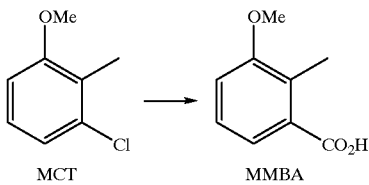

A 100 ml, 4-necked round bottomed flask equipped with a thermometer, condenser, nitrogen inlet and mechanical air stirrer was dried with a heat gun to remove any residual water due to moisture. All other glassware used in the reaction was dried by heat gun prior to use. The magnesium was charged and the flask and the magnesium were again dried using the heat gun. The anhydrous THF (40 ml) was added by syringe taking caution to avoid any exposure to water. To initiate the reaction and clean the surface of the magnesium, several drops (ca. 0.25 ml) of 1,2-dibromoethane were added, two pieces of magnesium turnings were broken (exposing a clean surface) and also added. The MCT was charged to a pressure equalizing addition funnel which had previously been dried. Approximately one third of the MCT was added to the flask. The reaction mixture was then heated with the heat gun to induce reflux. This procedure was repeated until a slight yellowing of the reaction solution was observed. The flask was then heated with an oil bath at 70° C., as the remaining MCT was charged slowly over a period of 20 minutes. The reaction was maintained at reflux during the formation of the Grignard reagent. The time to reach 96% conversion of the MCT to the Grignard reagent was about 8 hours.

After 8.5 hours, the reaction mixture was cooled with an ice bath and an additional 20 ml of anhydrous THF was charged. A 1000 ml flask was filled with dry ice pellets. The dry ice was sublimed and passed through a gas drying tower containing calcium sulfate. The dry $CO_2$ was bubbled through the reaction mixture while stirring. The reaction mixture became extremely viscous as the carboxylate salt of the product precipitated out. Carbon dioxide was allowed to bubble through the flask for about 2 hours.

About 115 ml of water was added to the carboxylated mixture and stirred for approximately 30 minutes. An extraction with ethyl acetate (3×50 ml) was done to remove any neutral organic compounds that remained. The combined organic layers were washed with saturated aqueous sodium bicarbonate solution (3×50 ml) to recover desired product. The organic layer was dried over $Na_2SO_4$, filtered and the solvents removed under reduced pressure. Both the water layer and the aqueous $NaHCO_3$ wash layer were acidified with concentrated HCl to pH 1. A white solid precipitated out in both layers. Each aqueous layer was separately extracted with ethyl acetate (3×100 ml). The organic ethyl acetate layers were combined, dried over $Na_2SO_4$, filtered and the solvent was removed under reduced pressure to give 19.3 g (81.8% yield) of desired MMBA product as an off white solid (mp 145°–147° C.).

TABLE 1

Charge Sheet for Example 8

| Component | MW | Mole | Equivalents | Charge |
|---|---|---|---|---|
| Mg | 24.31 | 0.157 | 1.11 | 3.82 gm |
| THF (d 0.889) | 72.11 | 0.493 | 3.47 | 40 ml |
| 1,2-dibromoethane | 187.87 | 0.003 | 0.020 | 0.25 ml |
| MCT | 156.61 | 0.142 | 1.00 | 22.2 gm |
| THF (2nd charge) | 72.11 | 0.247 | 1.74 | 20 ml |
| $CO_2$ | 44.01 | | | |
| $H_2O$ | 18.02 | | | 115 gm |
| Ethyl Acetate | 88.11 | | | 3 × 50 ml |
| aq. Sat'd. $NaHCO_3$ | 84.01 | | | 3 × 50 ml |
| conc. HCl (12M) | 36.46 | | | |
| 2nd Ethyl Acetate | 88.11 | | | 3 × 100 |
| 3rd Ethyl Acetate | 88.11 | | | 3 × 100 |
| anhydrous $Na_2SO_4$ | 142.04 | | | |

EXAMPLE 9

Grignard Reaction on 2,6-Dichlorotoluene (DCT) to Form 3-Chloro-2-Methylbenzoic Acid (CMBA)

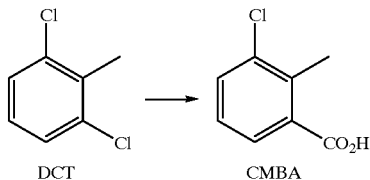

DCT (40 g) was charged to a flask with toluene (30 g). The mixture was azeotropically dried using a Dean-Stark trap. After water was completely removed, the solution was cooled.

A dry 250 mL, 4-necked round bottom flask equipped with a thermometer, condenser, nitrogen inlet, and stirrer was charged with magnesium (6.6 g) and anhydrous tetrahydrofuran (THF, 40 mL) and toluene (40 mL). Iodomethane (1 g) was added and the mixture stirred for 30 min at room temperature. The dry DCT/toluene solution from above was added, and the mixture heated to reflux (100–115° C.). After 4–5 hours the formation of the Grignard intermediate was complete.

The reaction mixture was cooled in an ice bath and additional THF (40 mL) was added. Solid carbon dioxide was sublimed through a gas drying tower containing calcium sulfate and bubbled into the reaction mixture with stirring. The reaction mixture became viscous as the salt of the CMBA precipitated from solution. Bubbling continued for 2 h.

Water (230 mL) was added and stirred 30 min. An extraction with ethyl acetate (100 mL) removed neutral impurities. The ethyl acetate layer was extracted with saturated aqueous sodium bicarbonate (100 mL). The bicarbonate layer and the remaining aqueous were combined and acidified to pH 1 with concentrated hydrochloric acid. A white precipitate resulted. The slurry was extracted with ethyl acetate (3×200 mL). The ethyl acetate layer was dried and the solvent removed under reduced pressure to yield CMBA (mp 202–204° C.).

EXAMPLE 10

Grignard Reaction on DCT to Form CMBA

A dry 250 mL, 4-necked round bottom flask equipped with a thermometer, condenser, nitrogen inlet, and stirrer was charged with magnesium (6.6 g) and anhydrous tetrahydrofuran (THF, 80 mL). Iodomethane (1 g) was added and the mixture stirred for 30 min at room temperature. Dry DCT/THF solution (40 g in 30 mL THF) was added, and the mixture heated to reflux (65–67° C.). After 4–8 hours, the formation of the Grignard intermediate was complete.

The reaction mixture was cooled in an ice bath and additional THF (40 mL) was added. Solid carbon dioxide was sublimed through a gas drying tower containing calcium sulfate and bubbled into the reaction mixture with stirring. The reaction mixture became viscous as the salt of the CMBA precipitated from solution. Bubbling continued for 2 h.

Water (230 mL) was added and stirred 30 min. An extraction with ethyl acetate (100 mL) removed neutral impurities. The ethyl acetate layer was extracted with saturated aqueous sodium bicarbonate (100 mL). The bicarbonate layer and the remaining aqueous were combined and acidified to pH 1 with concentrated hydrochloric acid. A white precipitate resulted. The slurry was extracted with ethyl acetate (3×200 mL). The ethyl acetate layer was dried and the solvent removed under reduced pressure to yield CMBA.

EXAMPLE 11

Reaction of CMBA with Sodium Methoxide to Form MMBA

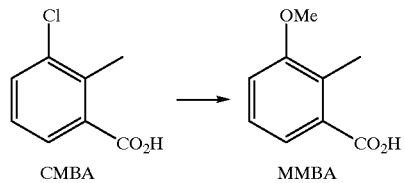

To a 3-necked flask equipped with a reflux condenser, a mechanical stirrer and a temperature controller is charged CMBA (450 g), DMSO (200 g) and powdered sodium methoxide (285 g). The mixture is purged with nitrogen, then is heated to 140–160° C. with stirring under a nitrogen blanket. The reaction is stopped when the residual CMBA is <10%, usually in 4–6 h. The mixture is then distilled under reduced pressure (15–20 mm Hg) using a 10-tray Oldershaw column, and about 200 g of distillate is removed. To the pot residue is added dimethyl sulfate (DMS, 18 g) and this mixture is held at 120° C. for 1 h. Water (400 mL) and ethyl acetate (400 mL) are added and the resulting mixture is stirred. After phase separation, the ethyl acetate layer is extracted with saturated aqueous sodium bicarbonate (100 mL). The aqueous phases are combined and are acidified to pH 1 with concentrated hydrochloric acid. The resulting slurry is extracted with ethyl acetate (2×200 mL). The combined ethyl acetate extracts are dried through sodium sulfate. Removal of solvent under reduced pressure yields MMBA.

EXAMPLE 12

Reaction of CMBA with Sodium Methoxide to Form MMBA

To a 3-necked flask equipped with a reflux condenser, a mechanical stirrer and a temperature controller is charged CMBA (450 g), DMSO (200 g), CuBr (13.5 g) and powdered sodium methoxide (285 g). The mixture is purged with nitrogen, then is heated to 140–160° C. with stirring under a nitrogen blanket. The reaction is stopped when the residual CMBA is <10%, usually in 4–6 h. The mixture is then distilled under reduced pressure (15–20 mm Hg) using a 10-tray Oldershaw column, and about 200 g of distillate is removed. To the pot residue is added dimethyl sulfate (DMS, 18 g) and this mixture is held at 120° C. for 1 h. Water (400 mL) and ethyl acetate (400 mL) are added and stirred. After phase separation, the ethyl acetate layer is extracted with saturated aqueous sodium bicarbonate (100 mL). The aqueous phases are combined and are acidified to pH 1 with concentrated hydrochloric acid. The resulting slurry is extracted with ethyl acetate (2×200 mL). The combined ethyl acetate extracts are dried through sodium sulfate. Removal of solvent under reduced pressure yields MMBA.

EXAMPLE 13

Reaction of CMBA with Sodium Hydroxide to Form 3-Hydroxy-2-Methylbenzoic Acid (HMBA)

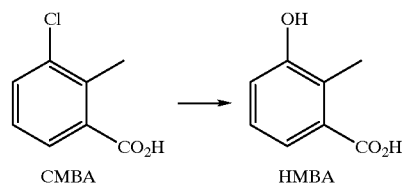

To a 3-necked flask equipped with a reflux condenser, a mechanical stirrer and a temperature controller is charged CMBA (450 g), DMSO (200 g) and powdered sodium hydroxide (247 g). The mixture is purged with nitrogen, then is heated to 140–160° C. with stirring under a nitrogen blanket. The reaction is stopped when the residual CMBA is <10%, usually in 4–6 h. The mixture is then distilled under reduced pressure (15–20 mm Hg) using a 10-tray Oldershaw column, and about 200 g of distillate is removed. After cooling to room temperature, water (400 mL) and ethyl acetate (400 mL) are added and the resulting mixture is stirred. After phase separation, the ethyl acetate layer is extracted with saturated aqueous sodium bicarbonate (100 mL). The aqueous phases are combined and are acidified to pH 1 with concentrated hydrochloric acid. The resulting slurry is extracted with ethyl acetate (2×200 mL). The combined ethyl acetate extracts are dried through sodium sulfate. Removal of solvent under reduced pressure yields HMBA (melting point 126–132° C.).

EXAMPLE 14

Reaction of CMBA with Sodium Hydroxide to Form HMBA

To a 3-necked flask equipped with a reflux condenser, a mechanical stirrer and a temperature controller is charged CMBA (450 g), DMSO (200 g), copper bromide (13.5 g) and powdered sodium hydroxide (247 g). The mixture is purged with nitrogen, then is heated to 140–160° C. with stirring under a nitrogen blanket. The reaction is stopped when the residual CMBA was <10%, usually in 4–6 h. The mixture is then distilled under reduced pressure (15–20 mm Hg) using a 10-tray Oldershaw column, and about 200 g of distillate is removed. After cooling to room temperature, water (400 mL) and ethyl acetate (400 mL) are added and the resulting mixture is stirred. After phase separation, the ethyl acetate layer is extracted with saturated aqueous sodium bicarbonate (100 mL). The aqueous phases are combined and are acidified to pH 1 with concentrated hydrochloric acid. The resulting slurry is extracted with ethyl acetate (2×200 mL). The combined ethyl acetate extracts are dried through sodium sulfate. Removal of solvent under reduced pressure yields HMBA.

EXAMPLE 15

Procedure for Converting MMBA to HMBA

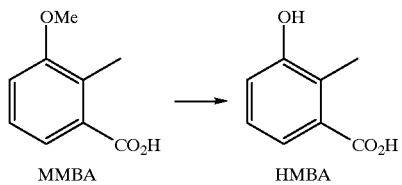

EXAMPLE 15A

To a 20 mL pressure tube was charged 0.50 g of 3-methoxy-2-methylbenzoic acid (3.0 mmol) and 1.52 g of 48% hydrobromic acid (9.0 mmol, 3.0 eq). The tube was sealed and heated to 170° C. in an oil bath. The mixture was stirred for 4 hours using a magnetic stirrer. It was then cooled to ambient temperature. A portion of the material was stripped to dryness under vacuum to remove volatile components. Analyses of the residue by GC and NMR showed that pure 3-hydroxy-2-methylbenzoic acid was obtained.

EXAMPLE 15B

To a 500 mL, 3-necked flask, equipped with a reflux condenser, a heating mantle, a scrubber, a stirrer, and an addition funnel, was charged 50 g of MMBA (0.30 mol) and 100 g of glacial acetic acid (1.67 mol). The mixture was heated to reflux (110° C.) and stirred until all the solid MMBA was dissolved. To the addition funnel was charged 152 g of 48% hydrobromic acid (0.90 mol), which was then added gradually to the reaction mixture over a period of three hours. The resulting mixture was stirred at reflux until the demethylation reaction was judged complete based on GC analysis. The mixture was stripped to dryness under vacuum (110° C., 100 mm Hg) to yield crude HMBA.

EXAMPLE 16

Procedure for Converting HMBA to 3-Acetoxy-2-methylbenzoic Acid (AMBA)

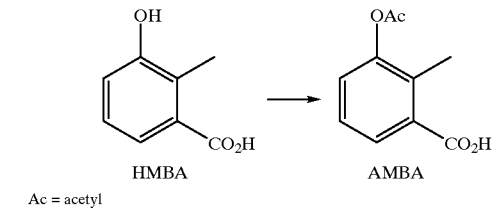

To a 50 mL, 3-necked flask, equipped with a reflux condenser, a heating source, a magnetic stirrer, and an addition funnel, were charged 5.00 g of 3-hydroxy-2-methylbenzoic acid (32.9 mmol), and 10 mL of ethyl acetate. The mixture was stirred at 30° C. until HMBA was dissolved. Acetic anhydride (7.50 g, 73.5 mmol) was then added through the addition funnel in 10 minutes. The resulting mixture was stirred at 50° C. for 30 hours. GC analysis showed that at the end of this period the composition of the mixture was (area % by FID): 3-acetoxy-2-methylbenzoic acid 93.32%, 3-hydroxy-2-methylbenzoic acid 0.13%.

EXAMPLE 17

Procedure for Converting HMBA to AMBA

To a 100 mL, 3-necked flask, equipped with a reflux condenser, a heating source, a magnetic stirrer, and an addition funnel, were charged 5.72 g of 3-hydroxy-2-methylbenzoic acid (37.6 mmol), 1.0 g of pyridine (12.6 mmol), and 20 mL of ethyl acetate. The mixture was stirred at ambient temperature until the 3-hydroxy-2-methylbenzoic acid was dissolved. Acetic anhydride (4.80 g, 47.0 mmol) was then added through the addition funnel in 10 minutes. The resulting mixture was stirred at 30° C. for 3 hours, and 50° C. for 2 hours. GC analysis showed that at the end of this period the composition of the mixture was (area % by FID): 3-acetoxy-2-methylbenzoic acid 96.52%, 3-hydroxy-2-methylbenzoic acid 0.52%.

EXAMPLE 18

Procedures for Converting MCT to 3-Methoxy-2-Methylbenzoyl Chloride (MMBC)

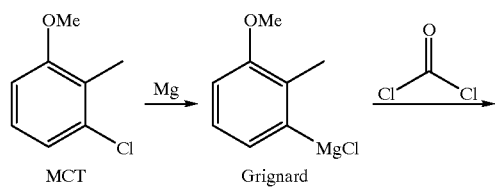

-continued

[Structure: MMBC - methoxy-methyl-benzoyl chloride]

EXAMPLE 18A

MCT (44.4 g) was charged to a flask with toluene (30 g). The mixture was azeotropically dried using a Dean-Stark trap. After the water was completely removed, the solution was cooled.

A dry 250 mL, 4-necked round bottom flask equipped with a thermometer, condenser, nitrogen inlet, and stirrer was charged with magnesium (7.6 g) and anhydrous tetrahydrofuran (THF, 40 mL) and toluene (40 mL). Iodomethane (3.5 g) was added and the mixture was stirred for 30 min at room temperature. The dry MCT/toluene solution from above was added, and the mixture heated to reflux (90–115° C.). After 8–10 hours, the formation of the Grignard intermediate was complete. The Grignard reagent was drawn up in a gas tight syringe and transferred to an addition funnel attached to a flask containing toluene (50 mL) and phosgene (30 g). The Grignard reagent was added dropwise to the phosgene solution over 30 min at 15–30° C., then stirred 4 h. The reaction mixture was filtered, and the filtrate distilled to yield recovered solvent, then MMBC (>30% yield).

EXAMPLE 18B

As in Example 18A above, except 33 g of phosgene used. MMBC was obtained in >30% yield.

EXAMPLE 18C

As in Example 18A above, except the Grignard mixture was added to phosgene at a temperature of 0–10° C. MMBC was obtained in >30% yield.

EXAMPLE 18D

As in Example 18A above, except 41 g of phosgene was used. The addition of Grignard to phosgene was carried out at −10° C. MMBC was obtained in >40% yield.

EXAMPLE 18E

As in Example 18A above, except 60 g of phosgene was used. The addition of Grignard to phosgene was carried out at −20° C. MMBC was obtained in >40% yield.

What is claimed is:

1. A process for the preparation of a compound of formula (VII) comprising the steps of (i) reacting a compound of formula (I) with an alkali or alkaline earth alkoxide, alkali or alkaline earth aroxide, alkali or alkaline earth arylalkoxide, or alkali or alkaline earth heteroarylalkoxide, optionally in the presence of a catalyst comprising copper, to form a compound of formula (IIa)

[Reaction scheme: (I) → (IIa)]

(ii) reacting a compound of formula (IIa) with magnesium metal using anhydrous conditions to form an intermediate compound of formula (IIb)

[Reaction scheme: (IIa) + Mg Metal, Solvent & Optional Initiator → (IIb)]

(iii) reacting the intermediate compound of formula (IIb) with phosgene to form a compound of formula (VII)

[Reaction scheme: (IIb) + phosgene → (VII)]

wherein each X is independently chloro, bromo or iodo;

R is a hydrogen atom, $(C_1-C_6)$alkyl, aryl, aryl$(C_1-C_2)$alkyl, heteroaryl or heteroaryl$(C_1-C_2)$alkyl; or a $(C_1-C_6)$alkyl, aryl, aryl$(C_1-C_2)$alkyl, heteroaryl or heteroaryl$(C_1-C_2)$alkyl substituted with from one to three substituents independently selected from $(C_1-C_3)$alkyl and $(C_1-C_3)$alkoxy;

$R^1$ is $CHR^2R^3$, aryl, aryl$(C_1-C_2)$alkyl or heteroaryl$(C_1-C_2)$alkyl; or aryl, aryl$(C_1-C_2)$alkyl or heteroaryl$(C_1-C_2)$alkyl substituted with from one to three substituents independently selected from $(C_1-C_3)$alkyl and $(C_1-C_3)$alkoxy; and $R^2$ and $R^3$ are each independently a hydrogen atom, $(C_1-C_5)$alkyl or $(C_1-C_3)$alkyl substituted with $(C_1-C_2)$alkoxy.

2. The process of claim 1 wherein each X is independently chloro or bromo;

R is a hydrogen atom or $(C_1-C_6)$alkyl;

$R^1$ is $CHR^2R^3$, aryl or aryl$(C_1-C_2)$alkyl; and $R^2$ and $R^3$ are each independently a hydrogen atom or $(C_1-C_2)$alkyl, or $(C_1-C_2)$alkyl substituted with methoxy.

3. The process of claim 2 wherein each X is chloro, R is a hydrogen atom or $(C_1-C_3)$alkyl, $R^1$ is $CHR^2R^3$, and $R^2$ and $R^3$ are each independently a hydrogen atom or $(C_1-C_2)$alkyl.

4. The process of claim 3 wherein R is methyl or ethyl, $R^2$ is a hydrogen atom, and $R^3$ is a hydrogen atom or methyl.

5. A process for the direct formation of an acyl chloride of formula (IX) by quenching a Grignard reagent of formula (VIII) with phosgene

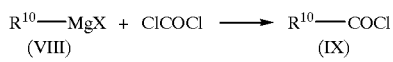

wherein $R^{10}$ is an organic radical selected from alkyl, aryl and aralkyl, and X is chloro, bromo or iodo.

6. The process of claim 1 wherein the phosgene is added to the Grignard intermediate at a temperature of −30 to 30° C. at ambient pressure.

7. The process of claim 1 wherein from 1.1 to 10 equivalents of phosgene is added per equivalent of Grignard intermediate.

* * * * *